US008612252B1

(12) United States Patent
Gravina

(10) Patent No.: US 8,612,252 B1
(45) Date of Patent: Dec. 17, 2013

(54) CARE MANAGEMENT AND TRANSPORTATION WORKFLOW

(75) Inventor: Craig S. Gravina, Farmington, CT (US)

(73) Assignee: Allscripts Software, LLC, Chicago, IL (US)

( * ) Notice: Subject to any disclaimer, the term of this patent is extended or adjusted under 35 U.S.C. 154(b) by 0 days.

(21) Appl. No.: 13/372,181

(22) Filed: Feb. 13, 2012

Related U.S. Application Data

(63) Continuation-in-part of application No. 12/392,968, filed on Feb. 25, 2009.

(60) Provisional application No. 61/031,354, filed on Feb. 25, 2008.

(51) Int. Cl.
  *G06Q 10/00* (2012.01)
  *G06Q 50/00* (2012.01)
(52) U.S. Cl.
  USPC .................................................. 705/2; 705/3
(58) Field of Classification Search
  USPC ..................... 705/2–3; 340/539.11; 704/270
  See application file for complete search history.

(56) References Cited

U.S. PATENT DOCUMENTS

| | | | |
|---|---|---|---|
| 2002/0010679 A1* | 1/2002 | Felsher | 705/51 |
| 2002/0072911 A1* | 6/2002 | Kilgore et al. | 704/270 |
| 2006/0049936 A1* | 3/2006 | Collins et al. | 340/539.11 |
| 2007/0143143 A1* | 6/2007 | Villasenor et al. | 705/2 |

OTHER PUBLICATIONS

Conexsys HI-IQ TouchSchedule, Dec. 2006.*

* cited by examiner

*Primary Examiner* — Joseph Burgess
(74) *Attorney, Agent, or Firm* — Tillman Wright, PLLC; Chad D. Tillman; Jeremy C. Doerre

(57) ABSTRACT

A system for facilitating the provision of health care services to patients comprises a computer-readable medium containing information associated with the provision of health care services to patients; an electronic display disposed in a health care environment; and software configured to effect display of some of the information on the electronic display. A method for facilitating the provision of health care services to patients comprises inputting, via an electronic touch screen display, information corresponding to a patient or room; displaying, via the electronic touch screen display, the information; and providing, to a patient, physical health care services, based on the viewed information. The electronic touchscreen display preferably is not a part of a computer workstation and is configured for simultaneous viewing by a plurality of health care providers and caregivers.

15 Claims, 3 Drawing Sheets

Nursing Unit Whiteboard

WHITE 10 CENSUS BOARD

| ROOM | PATIENT | PRIMARY TEAM | PRECAUTIONS/TEAM | | TODAY'S NURSE |
|---|---|---|---|---|---|
| 12 A | | | MRSA | C | Kelly |
| 12 B | | | MRSA | C | Carol |
| 14 A | | | VRE | C | ZARA |
| 14 B | | Ella / Erica Rachel / Cristina | VRE/CMV+ | C | Courtney |
| 16 | | | MRSA/VRE | C | Carol |
| 18 | | | Social Isolation | C | Courtney |
| 20 A | | | | C | Kelly |
| 22 A | | | | C | Jen |
| 22 B | | | | C | ZARA |
| 28 A | | | | C | Courtney |
| 28 B | | | | C | Leah |
| 30 A | | | | C | Jen |
| 30 B | | | | C | Rachel |
| 32 | | | MRSA/VRE | C | Leah |
| 34 | | | C-DIFF | C | Rachel |
| 36 A | | | VRE | C | Leah |
| 36 B | | Cristina | VRE | C | Rachel |
| 38 A | | Michelle | | C | Carol |
| 38 B | | | | C | Kelly |

Restraint   Sitter   VRE   Resource Nurse Colleen
Bed Alarm
Fall Risk

- Patient/Room assignments
- Patient precautions
- Nurse assignments
- Unit Memos

Travel Board

Pending Admissions
Name, MRX, Gender, Diagnoses, RN assigned, bed assignment, where patient is coming from Xxx xx xxxxx xxxx xxx xxx...0..0
Xxx xxxx xxxxx
xxx xx xxxxx
xxx xx xxxxx xxxx xxx xxx..0..0
xxx xx xxxxx xxxx xxx xxx..0..0
Xxx xxxx xxxxxx xxx...0..0
xxx xx xxxxx xxxx xxx xxx..0..0
xxx xx xxxxx xxxx xxx xxx..0..0

Monitor all staff here

DISCHARGE INSTRUCTIONS
xx xxxxx xxx ...0..0
Xxx xxxx xxx ...0..0
Xxx xx xxxxx xxxx xxx xxx..0..0
x xx xxxxx xxx..0..0
x xx xxxxx xxxx xxx..0..0
x xx xxxxx xxx..0..0
xxx xx xxxxx xxxx xxx xxx..0..0
xxx xx xxxxx xxxx xxx xxx..0..0
Room Nurce, Line of DC/TX & 2 check boxes — pt Dced, bed cleared

BED MOVES

- Patients off floor w/location
- Bed cleaning status
- Pending admissions
- Pending Discharges & Transfers

FIG. 1

CARE MANAGEMENT AND TRANSPORTATION WORKFLOW

CROSS-REFERENCE TO RELATED APPLICATION

The present application is a U.S. continuation-in-part patent application of, and claims priority under 35 U.S.C. §120 to, U.S. nonprovisional patent application Ser. No. 12/392,968, filed Feb. 25, 2009, which nonprovisional patent application published as U.S. patent application publication no. 2009/0254365, which patent application and any patent application publications thereof, including the above-noted patent application publication, are hereby incorporated herein by reference, which '968 application is a U.S. nonprovisional patent application of, and claims priority under 35 U.S.C. §119(e) to, U.S. provisional patent application No. 61/031,354, filed Feb. 25, 2008, which is incorporated herein by reference. The disclosure of provisional patent application No. 61/031,354 further is attached hereto as Exhibit 1, which is hereby incorporated herein by reference. The present application also incorporates herein by reference Exhibits 2-7 attached hereto, as well as U.S. patent application publication no. 2003/0074222.

COPYRIGHT STATEMENT

All of the material in this patent document, including the computer program listing, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

Computer Program Listing

Submitted concurrently herewith via the USPTO's electronic filing system (EFS), and incorporated herein by reference, is a computer program listing illustrating instructions, routines, and/or other contents of one or more computer programs. A first subset of this listing is associated with a proof of concept application and is in the form of two .txt files. The first file is named "prog.txt", has a file size of 13,573,266 bytes, and a creation date of Feb. 23, 2009 9:21:24 PM. The second file is named "demo.txt", has a file size of 24,480,752 bytes, and a creation date of Feb. 23, 2009 9:22:31 PM. A second subset of this listing is associated with a subsequently developed application and is in the form of two .txt files as well. The first file is named "careone.txt", has a file size of 11,169,756 bytes, and a creation date of Feb. 25, 2009 5:23:02 PM. The second file is named "caretwo.txt", has a file size of 21,609,460 bytes, and a creation date of Feb. 25, 2009 5:26:51 PM. A third .txt file that allows the pertinent information from the two .txt files of each subset to be extracted is included. This third .txt file is named "ascify.txt", has a file size of 37,475 bytes, and a creation date of Feb. 25, 2009 11:21:33 AM. A fourth .txt file, "readme.txt", which has a file size of 4,371 bytes and a creation date of Feb. 23, 2009 9:21:24 PM, includes instructions on how to use "ascify.txt" to convert the other text files into a format that can be easily explored and understood by one having ordinary skill in the art.

BACKGROUND OF THE INVENTION

The present invention generally relates to a system for care visibility for use in a health care environment, such as a hospital.

The health care industry, like many industries, grows more and more dependent on information each year. The information that is available to hospital staff at any given time will have a marked impact on the efficiency and level of care received by patients. Increasing the amount of information available to staff, as well as increasing the ease of obtaining this information, will help to optimize workflow throughout the hospital and will facilitate the actual provision of health care to patients.

Specifically, nurses and other critical support staff currently spend a large amount of time trying to obtain information that will allow them to perform their job effectively. If their awareness of this information was increased, by allowing them easier access to relevant information in more locations throughout the hospital, then they would become more efficient, workflow throughout the hospital would be further optimized, and the provision of health care to patients would be facilitated.

Currently, various systems may be used in a health care environment, such as, for example, a system that monitors various conditions of a plurality of hospital beds located in different rooms of a healthcare facility as disclosed in USPA Pub. No. 2006/0049936 to Collins. This publication is hereby incorporated into the present application by reference strictly for purposes of background.

A need exists for improvement in systems for care visibility for use in a health care environment. This, and other needs, are addressed by one or more aspects of the present invention.

SUMMARY OF THE INVENTION

The present invention includes many aspects and features. Moreover, while many aspects and features relate to, and are described in, the context of a health care environment, the present invention is not limited to use only in a health care environment, as will become apparent from the following summaries and detailed descriptions of aspects, features, and one or more embodiments of the present invention.

Accordingly, one aspect of the present invention relates to a computer-implemented system for facilitating the provision of physical health care service to patients. The system includes a computer-readable medium containing information associated with the physical provision of health care; an electronic display disposed in a health care environment; software stored in a computer-readable medium, the software being configured to effect display of some of the information on the electronic display in a tabular view. The electronic display is not a part of a computer workstation and is configured for simultaneous viewing by a plurality of staff.

In a feature of this aspect of the invention, the tabular view is configured to resemble a nursing unit whiteboard.

In a feature of this aspect of the invention, the system further comprises a nursing unit whiteboard and the electronic display supplements the whiteboard.

In a feature of this aspect of the invention, the electronic display is disposed adjacent the whiteboard.

In a feature of this aspect of the invention, the software is further configured to effect display of some of the information on the electronic display in a floor plan view.

In a feature of this aspect of the invention, the system further comprises a computer workstation for entry of information.

In a feature of this aspect of the invention, the electronic display comprises a liquid crystal display (LCD).

In a feature of this aspect of the invention, the electronic display comprises a plasma display.

In a feature of this aspect of the invention, the electronic display comprises an LCD monitor.

In a feature of this aspect of the invention, the electronic display comprises an LCD television.

In a feature of this aspect of the invention, the electronic display comprises a plasma television.

In a feature of this aspect of the invention, the electronic display comprises a projection display device.

In a feature of this aspect of the invention, the electronic display comprises a flat panel display.

In a feature of this aspect of the invention, the electronic display is mounted to a wall.

In a feature of this aspect of the invention, the information comprises data corresponding to a plurality of patients, beds, or rooms.

In a feature of this aspect of the invention, the data includes patient locations.

In a feature of this aspect of the invention, the data includes patient attributes.

In a feature of this aspect of the invention, the data includes room attributes.

In a feature of this aspect of the invention, the data includes bed attributes.

In a feature of this aspect of the invention, the data includes information related to care of a patient.

In a feature of this aspect of the invention, the electronic display is disposed behind a nurses' station.

In a feature of this aspect of the invention, the electronic display is disposed in a patient room.

In a feature of this aspect of the invention, the electronic display is disposed in a hallway.

In a feature of this aspect of the invention, the software is configured to display, via the electronic display, information related to various workflows associated with admissions of patients to the health care environment.

In a feature of this aspect of the invention, the software is configured to display, via the electronic display, information related to various workflows associated with discharges of patients from the health care environment.

In a feature of this aspect of the invention, the software is configured to display, via the electronic display, information related to various workflows associated with transfers of patients within the health care environment.

In a feature of this aspect of the invention, the software is configured to display, via the electronic display, information related to various workflows associated with housekeeping of patient rooms.

In a feature of this aspect of the invention, the software is configured to display, via the electronic display, information related to various workflows associated with housekeeping of patient beds.

In a feature of this aspect of the invention, the software is configured to display, via the electronic display, information related to various workflows associated with transportation of patients within the health care environment.

In a feature of this aspect of the invention, the software is configured to display, via the electronic display, information related to various workflows associated with transportation of patients to another health care environment.

In a feature of this aspect of the invention, the software is configured to display, via the electronic display, a metric corresponding to a nurse to patient assignment ratio.

In a feature of this aspect of the invention, the software is configured to display, via the electronic display, a metric corresponding to unit occupancy.

In a feature of this aspect of the invention, the software is configured to display a metric corresponding to pending admissions.

In a feature of this aspect of the invention, the software is configured to display, via the electronic display, a metric corresponding to pending discharges.

In a feature of this aspect of the invention, the software is configured to display, via the electronic display, a metric corresponding to pending transfers.

In a feature of this aspect of the invention, the software is configured to display, via the electronic display, a clinical indicator associated with a patient.

In a feature of this aspect of the invention, the system is integrated with an external system which stores clinical information, and wherein the software is configured to display the stored clinical information on the electronic display.

In a feature of this aspect of the invention, the electronic display comprises an electronic touch screen display.

In another feature, the electronic touch screen display allows a user to interact via touch screen input with various workflows.

Another aspect of the present invention relates to a computer-implemented system for facilitating the physical provision of health care services to a plurality of patients. The system includes a computer-readable medium containing information associated with the physical provision of health care services to patients; an electronic display disposed in a health care environment; and software stored in a computer-readable medium, the software being configured to effect display of some of the information on the electronic display in a floor plan view. In this aspect, the electronic display is not a part of a computer workstation and is configured for simultaneous viewing by a plurality of staff.

Another aspect of the present invention relates to a computer-implemented system for facilitating the physical provision of health care services to a plurality of patients. The system includes a computer-readable medium containing information associated with the physical provision of health care services to patients; an electronic display disposed in a health care environment; software stored in a computer-readable medium, the software being configured to effect display of some of the information on the electronic display in both a tabular view and a floor plan view. In this aspect, the electronic display is not a part of a computer workstation and is configured for simultaneous viewing by a plurality of staff.

Another aspect of the present invention relates to a computer-implemented method for facilitating the physical provision of health care services to a plurality of patients. The method includes receiving, at an electronic touch screen display, information stored in a computer-readable medium associated with the physical provision of health care services to patients; viewing, simultaneously by a plurality of staff at the electronic touch screen display, the information; and providing, to a patient, physical health care services, based on the viewed information. In this aspect, the electronic touch screen display is not a part of a computer work station.

Another aspect of the present invention relates to a computer-implemented method for facilitating the physical provision of health care services to a plurality of patients. The method includes receiving, at an electronic touch screen display, information stored in a computer-readable medium associated with the physical provision of health care services to patients; inputting, via the electronic touch screen display, a milestone; and viewing, simultaneously by a plurality of staff at the electronic touch screen display, an indication of the milestone. In this aspect, the electronic touch screen display is not a part of a computer work station.

In a feature of this aspect of the invention, the milestone is a discharge milestone.

Another aspect of the present invention relates to a computer-implemented method for facilitating the physical provision of health care services to a plurality of patients. The method includes receiving, at an electronic touch screen display, information stored in a computer-readable medium associated with the physical provision of health care services to patients; displaying, on the electronic touch screen display, some of the received information; receiving a milestone input via the electronic touch screen display; storing data representative of the milestone in a computer-readable medium; and displaying, on the electronic touch screen display, an indication of the milestone. In this aspect, the electronic touch screen display is not a part of a computer workstation and is configured for simultaneous viewing by a plurality of staff.

Another aspect of the present invention relates to a computer-implemented method for facilitating the physical provision of health care services to a plurality of patients. The method includes receiving, at an electronic touch screen display, information stored in a computer-readable medium associated with the physical provision of health care services to patients; inputting, via the electronic touch screen display, a milestone; and automatically alerting a particular user upon completion of the milestone. In this aspect, the electronic touch screen display is not a part of a computer work station.

In a feature of this aspect, automatically alerting a particular user comprises automatically sending a text message to a number associated with the particular user.

In a feature of this aspect, the number is a phone number.

In a feature of this aspect, the number is a pager number.

Another aspect of the present invention relates to a computer-implemented method for facilitating the physical provision of health care services to a plurality of patients. The method includes receiving, at an electronic touch screen display, information stored in a computer-readable medium associated with the physical provision of health care services to patients; displaying, on the electronic touch screen display, some of the received information; receiving a milestone input via the electronic touch screen display; storing data representative of the milestone in a computer-readable medium; and automatically alerting a particular user upon completion of the milestone; wherein In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; requesting, via the electronic touch screen display, housekeeping of a patient's room or bed; and monitoring, using the electronic touch screen display, a status of the request. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, on the electronic touch screen display, some of the received information; receiving a request for housekeeping of a patient's bed or room input via the electronic touch screen display; storing data representative of the request in a computer-readable medium; and displaying, on the electronic touch screen display, an indication of the request together with a status of the request. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; inputting, via the electronic touch screen display, a request for housekeeping of a patient's bed or room; and automatically alerting a particular user upon completion of housekeeping of the patient's bed or room. In this aspect, the electronic touch screen display is not a part of a computer work station.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, on the electronic touch screen display, some of the received information; receiving a request for housekeeping of a patient's bed or room input via the electronic touch screen display; storing data representative of the request in a computer-readable medium; and automatically alerting a particular user upon completion of housekeeping of the patient's bed or room. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; requesting, via the electronic touch screen display, a request for transportation of a patient; and monitoring, using the electronic touch screen display, a status of the request. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, on the electronic touch screen display, some of the received information; receiving a request for transportation of a patient input via the electronic touch screen display; storing data representative of the request in a computer-readable medium; and displaying, on the electronic touch screen display, an indication of the request together with a status of the request. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; inputting, via the electronic touch screen display, a request for transportation of a patient; and automatically alerting a particular user upon completion of transportation of the patient. In this aspect, the electronic touch screen display is not a part of a computer work station.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, on the electronic touch screen display, some of the received information; receiving a request for transportation of a patient input via the electronic touch screen display; storing data representative of the request in a computer-readable medium; and automatically alerting a particular user upon completion of transportation of the patient. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium representative of an arrival of a patient; displaying, via the electronic touch screen display, an indicator of the arrival of the patient; selecting, via the electronic touch screen display, a room for the patient; storing, in a computer-readable medium, an association of the patient with the room for the patient; and displaying, in a floor plan view via the electronic touch screen display, the association of the patient with the room for the patient. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium representative of an arrival of a patient; displaying, via the electronic touch screen display, an indicator of the arrival of the patient; receiving a selection of a room for the patient, the selection having been input via the electronic touch screen display; storing, in a computer-readable medium, an association of the patient with the room for the patient; and displaying, in a floor plan view via the electronic touch screen display, the association of the patient with the room for the patient. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium representative of staff assigned to care of a patient; displaying, via the electronic touch screen display, an indication of the staff assigned to care of the patient; selecting, via the electronic touch screen display, a staff member to assign to care of the patient; storing, in a computer-readable medium, an association of the staff member with the patient; and displaying, via the electronic touch screen display, the association of the staff member with the patient. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium representative of staff assigned to care of a patient; displaying, via the electronic touch screen display, an indication of the staff assigned to care of the patient; receiving a selection of a staff member for care of the patient, the selection having been input via the electronic touch screen display; storing, in a computer-readable medium, an association of the staff member with the patient; and displaying, via the electronic touch screen display, the association of the staff member with the patient. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, in a floor plan view via the electronic touch screen display, the information; displaying, in response to an input via the electronic touch screen display, the information in a tabular view; and providing, to a patient, health care services, based on the viewed information. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, in a tabular view via the electronic touch screen display, the information; displaying, in response to an input via the electronic touch screen display, the information in a floor plan view; and providing, to a patient, health care services, based on the viewed information. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, in a floor plan view via the electronic touch screen display, the information; displaying, in response to an input via the electronic touch screen display, the information in a tabular view; and providing, to a patient, health care services, based on the viewed information. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes receiving, at an electronic touch screen display, information stored in a computer-readable medium associated with the physical provision of health care services to patients; displaying, in a floor plan view via the electronic touch screen display, the information; inputting, via the electronic touch screen display, a request to display the information in a tabular view; displaying, via the electronic touch screen display, the information in a tabular view; and providing, to a patient, health care services, based on the viewed information. In this aspect, the electronic touch screen display is not a part of a computer workstation and is configured for simultaneous viewing by a plurality of staff.

Another aspect of the present invention relates to a computer-implemented method for facilitating the physical provision of health care services to patients. The method includes inputting, via a first electronic touch screen display, information for use in the provision of health care displaying, at a second electronic touch screen display, the information; viewing, simultaneously by a plurality of staff at the second electronic touch screen display, the information; and providing, to a patient, health care services, based on the viewed information. The electronic touch screen displays are not a part of a computer work station.

Another aspect of the present invention relates to a computer-implemented method for facilitating the physical provision of health care services to patients. The method includes inputting, via a first electronic touch screen display, information for use in the provision of health care; displaying, at a plurality of touch screen displays, the information; viewing, simultaneously by a plurality of staff at one of the plurality of electronic touch screen displays, the information; and providing, to a patient, health care services, based on the viewed information. The electronic touch screen displays are not a part of a computer work station.

In a feature of this aspect, the first electronic touch screen display is one of the plurality of touch screen displays.

Another aspect of the present invention relates to a computer-implemented method for facilitating the physical provision of health care services to patients. The method includes inputting, via a computer workstation, information for use in the provision of health care displaying, at an electronic touch screen display, the information; viewing, simultaneously by a plurality of staff at the electronic touch screen display, the information; and providing, to a patient, health care services, based on the viewed information. The electronic touch screen displays are not a part of a computer work station.

Another aspect of the present invention relates to a system comprising computer-implemented means for facilitating the provision of physical health care services by health care providers in a hospital or hospital-like environment to patients, wherein physical health care services are provided to patients based on said means.

Another aspect of the present invention relates to a method comprising a computer-implemented step of facilitating the provision of health care services by health care providers in a hospital or hospital-like environment, and providing the health care services based thereon.

In addition to the aforementioned aspects and features of the present invention, it should be noted that the present invention further encompasses the various possible combinations and subcombinations of such aspects and features.

BRIEF DESCRIPTION OF THE DRAWINGS

One or more preferred embodiments of the present invention now will be described in detail with reference to the accompanying drawings, wherein, FIG. 1 depicts a conventional nursing unit whiteboard and travel board;

DETAILED DESCRIPTION

Figure 2:
FIG. 2 is a screenshot of an exemplary whiteboard view of data corresponding to patients or rooms in accordance with one or more aspects of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Finally, it will be appreciated that the physical provision of medical services can include, but is not limited to: conducting a physical exam, such as an eye, ear, nose, or throat exam; listening to a patient's heart or breathing, such as with a stethoscope; testing a patient's reflexes, such as with a rubber mallet; administering medicine, such as with a syringe, or orally, or topically; obtaining bodily material for testing, such as by drawing blood or taking a throat culture; conducting lab tests on bodily material; conducting an examination utilizing medical equipment, such as by use of x-ray or magnetic resonance imaging (MRI) equipment; transporting a patient, such as on a stretcher or in a wheelchair; cleaning an area in which a patient was present in the past or will be present in the future, such as by sanitizing an area or removing a bedpan; treating a patient, for example, via surgery; hooking a patient up on an IV; and admitting patient into a room at a heath care facility, including the physical processing and intake of the patient.

Referring now to the drawings, one or more preferred embodiments of the present invention are next described. The following description of one or more preferred embodiments is merely exemplary in nature and is in no way intended to limit the invention, its implementations, or uses.

FIG. 1 illustrates a conventional nursing unit whiteboard and travel board used in a health care environment. In preferred embodiments, such conventional whiteboards are replaced or supplemented with one or more electronic, interactive displays that integrate care delivery/clinical data from multiple sources into a common system. Preferably, this system comprises a care visibility, or care management, module that offers a web-native, enterprise-wide communications and visual alerting solution that drives coordinated clinical workflow and improves resource utilization across the entire care delivery process, thus allowing health care staff to more effectively prioritize work, manage patient care, and provide health care services to patients. This system preferably displays data in either a whiteboard view, loosely resembling a conventional whiteboard, or in a floor plan view. Each view preferably includes two or more variants, such as, for example, a medium view, which displays some data corresponding to a patient or room, and a large view, which displays all data corresponding to a patient or room.

In the whiteboard view, data is displayed in a tabular fashion. Each row displays data corresponding to a patient or room. Clicking on any row effects display of more detailed data corresponding to the patient or room associated with that row. FIG. 2 illustrates an exemplary whiteboard view in accordance with a system of the present invention.

Figure 3:
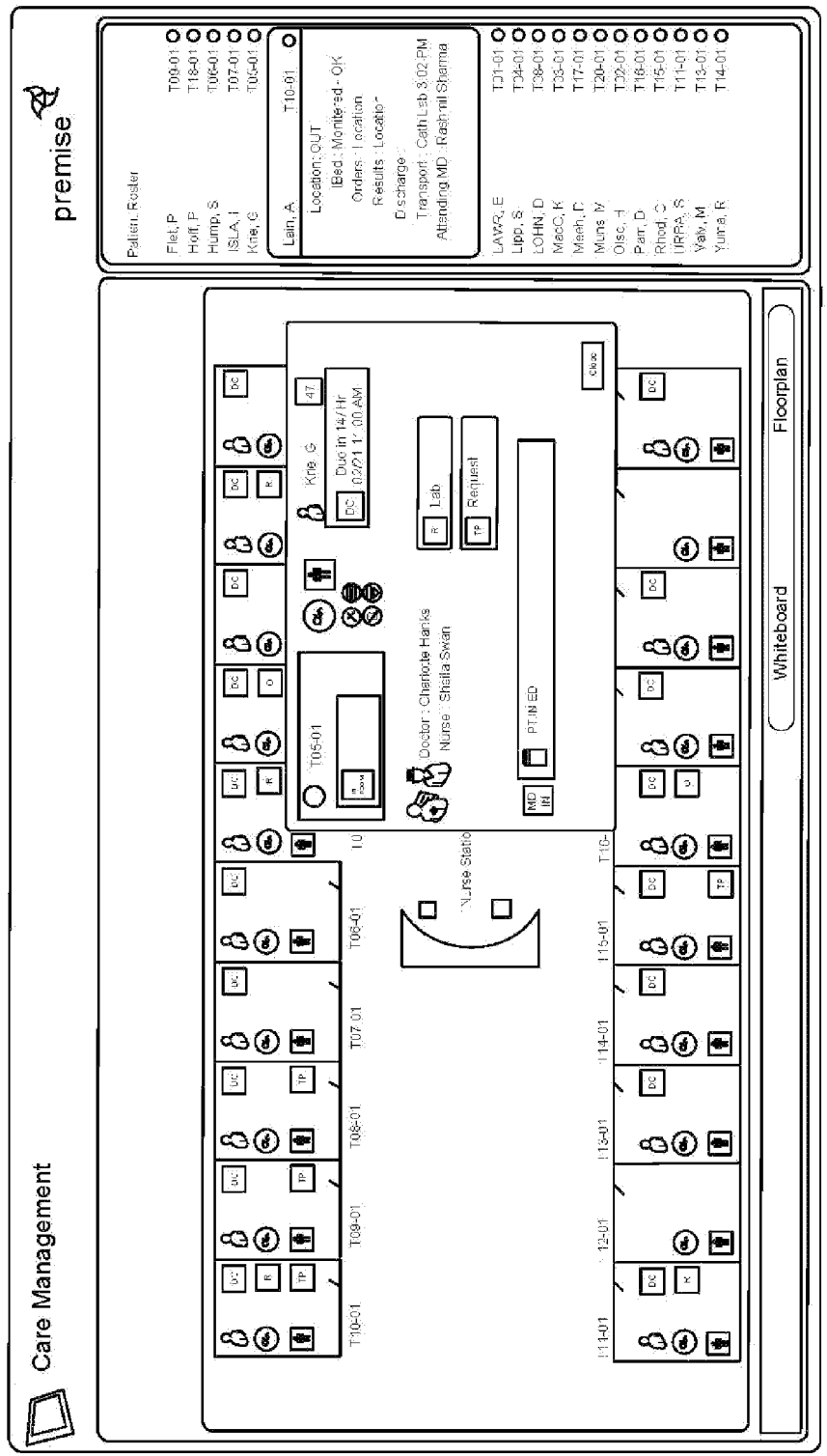
FIG. 3 is a screenshot of an exemplary floor plan view of data corresponding to patients or rooms in accordance with one or more aspects of the present invention.

In the floor plan view, data corresponding to patients or rooms is displayed in a manner akin to a floor plan. A patient roster, sorted alphabetically by name, is displayed on a side of the screen as illustrated in the exemplary floor plan view of FIG. 3. From this floor plan view, clicking on a patient's name in this patient roster effects display of a popup window containing key information corresponding to that patient. Clicking on a "details" buttons effects display of another popup window containing data corresponding to that patient on top of the room associated with that patient displayed in the floor plan view.

In at least one preferred embodiment, the electronic displays comprise touch-screen displays, and the system comprises software which provides health care staff with secure and HIPPA-compliant access to information.

Whether embodied in touch screens or otherwise, at least one implementation increases staff awareness of patient status and needs by increasing visibility of information related to patients on a nursing floor, in an emergency room or operating room, or in other areas of a hospital, such that a greater level and quality of health care services may be provided over conventional systems that utilize the whiteboard and travel board of FIG. 1.

For example, the system preferably increases the availability of access to Clinical Physician Order Entry (CPOE) systems by providing increased visibility along with alerts and notifications, and eliminating the need to go to other systems that may be located elsewhere. Similar integration provides increased visibility, alerts, and notifications for other external systems.

The system preferably integrates with bed management systems, such as those bed management systems provided by Premise Corporation of Farmington, Conn., and allows for the use of such systems without the need to go behind a desk or utilize a traditional work station. In at least one embodiment, this is accomplished by placing large, flat touchscreen panels behind nurses' stations, as well as in patient rooms and/or in hallways.

In at least one embodiment, some or all of the information—including potential alerts and notifications—is available over mobile devices, or communicated to mobile devices.

More specifically, one or more preferred systems in accordance with the present invention allow for:
a. Notification of incoming patients to a floor or unit.
b. Notification, tracking, and management of available, closed, and occupied beds.
c. Awareness and information related to patients within specific rooms/beds.
d. Requests for transports from one location to another within the hospital and automatic notification to dispatch upon such requests.
e. Status information related to transports, anticipated wait time, current location, pending within "x" time, overdue, in progress, etc.
f. Support staff updates and interactions with transport jobs.
g. Information related to bed status regarding cleanliness.
h. Support staff interaction with bed status.
i. Information related to discharge of patients.
j. Compiling of a list of necessary items to be accomplished before a patient may be discharged.
k. Requests for patient transfers, and accompanying visibility, alerts, notifications, and status updates.

Additional Disclosure of the Invention: Reference to Other Documents

Additional disclosure of aspects and features of the present invention is made now by reference to the Exhibits attached hereto, which Exhibits include documents which have been prepared throughout development of preferred systems of the invention, each Exhibit being hereby incorporated herein by reference in its entirety.

Exhibit 1 consists of 94 pages and includes the disclosure of U.S. provisional patent application No. 61/031,354, which itself includes the following appendices:

Appendix A comprises an innovation partner program care management model document, which includes a general summary of a described project for development of a care visibility, or care management, module;

Appendix B comprises a software requirements specification document for a care management proof of concept application and a transportation workflow proof of concept application;

Appendix C comprises a high level design document outlining high level design goals for a care visibility, or care management, application;

Appendix D comprises a care management interfaces document, which sets out desired elements of interfaces of a care visibility, or care management, system.

Appendix E comprises a bed management system/care management product separators document which distinguishes a care visibility, or care management, module from an underlying bed management system.

Appendix F comprises release notes from an early build of a proof of concept application.

Exhibit 2 consists of 5 pages and includes a hardware requirements document that sets forth hardware requirements and preferred architecture for a care visibility system in accordance with one or more preferred embodiments.

Exhibit 3 consists of 21 pages and includes a product plan document which sets forth, inter alia, functional requirements for a care visibility system in accordance with one or more preferred embodiments.

Exhibit 4 consists of 4 pages and includes a chart setting forth functional capabilities of two care visibility systems in accordance with one or more preferred embodiments.

Exhibit 5 consists of 31 pages and includes a slideshow disclosing aspects and features of a care visibility system in accordance with preferred embodiments.

Exhibit 6 consists of 1 page and includes an exemplary screenshot of a care visibility system in accordance with one or more preferred embodiments.

Exhibit 7 consists of 2 pages and includes a marketing document disclosing aspects and features of a care visibility system in accordance with one or more preferred embodiments.

Based on the foregoing description, and the disclosure of the attached Exhibits, it will be readily understood by those persons skilled in the art that the present invention is susceptible of broad utility and application. Many embodiments and adaptations of the present invention other than those specifically described herein and in the Exhibits, as well as many variations, modifications, and equivalent arrangements, will be apparent from or reasonably suggested by the present invention and the foregoing descriptions and disclosures thereof, without departing from the substance or scope of the present invention.

Accordingly, while the present invention has been described in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for facilitating the physical provision of health care services to a plurality of patients, the method comprising:
   (a) aggregating, at one or more electronic devices, information associated with the provision of health care services to patients from one or more systems, including an admission/discharge/transfer system and a bed management system;
   (b) displaying, via software, at an electronic touch-screen display, some of the aggregated information, the software being configured to
      (i) display information associated with a housekeeping status of one or more beds in a health care environment, and allow a user to edit the displayed information associated with the housekeeping status of such one or more beds,
      (ii) allow a first administrative user associated with a health care facility to define a list of discharge milestones and indicate that one or more of the defined discharge milestones are required for all patients within the health care facility,
      (iii) allow additional administrative users each associated with a respective unit of the health care facility to each select, from the discharge milestones defined by the first administrative user, milestones specific to a particular unit,
      (iv) display information associated with a planned discharge time,
      (v) display information associated with one or more defined discharge milestones for each one of a plurality of patients, and allow a user to edit the displayed information associated with one or more discharge milestones for one or more patients,
      (vi) display information in both a floor plan view and a tabular view,
      (vii) display information regarding the identity of one or more health care providers assigned to a patient, and allow a user to edit the displayed information regarding the identity of one or more health care providers assigned to a patient:
      (viii) determine discharge milestones used most frequently on a unit of the healthcare facility and display, to a user, a report conveying the determined discharge milestones, and
      (ix) determine the average time to completion of a discharge milestone compared to a planned discharge time and display, to a user, the determined average time to completion;
   (c) receiving authentication information;
   (d) validating the received authentication information;
   (e) receiving, via the electronic-touch screen display, user input related to some of the displayed information associated with the provision of health care services to patients; and
   (f) displaying, via the electronic touch-screen display, updated information associated with the provision of health care services to patients, the updated information being updated based at least in part on the received user input;
   (g) wherein the electronic touch-screen display is not a part of a computer work station.

2. The method of claim 1, wherein said step of receiving authentication information comprises receiving, via an electronic card reader, authentication information.

3. The method of claim 1, wherein the tabular view is configured to resemble a nursing unit whiteboard.

4. The method of claim 1, wherein a nursing unit whiteboard is disposed adjacent the electronic touch-screen display.

5. The method of claim 1, wherein the electronic touch-screen display is mounted to a wall.

6. A method for facilitating the physical provision of health care services to a plurality of patients, the method comprising:
   (a) aggregating, at one or more electronic devices, information associated with the provision of health care services to patients from one or more systems, including an admission/discharge/transfer system and a bed management system;

(b) displaying, via software, at an electronic touch-screen display, some of the aggregated information, the software being configured to
  (i) display information associated with a housekeeping status of one or more beds in a health care environment, and allow a user to edit the displayed information associated with the housekeeping status of such one or more beds,
  (ii) allow a first administrative user associated with a health care facility to define a list of discharge milestones and indicate that one or more of the defined discharge milestones are required for all patients within the health care facility,
  (iii) allow additional administrative users each associated with a respective unit of the health care facility to each select, from the discharge milestones defined by the first administrative user, milestones specific to a particular unit,
  (iv) display information associated with a planned discharge time,
  (v) display information associated with one or more defined discharge milestones for each of a plurality of patients, and allow a user to edit the displayed information associated with one or more discharge milestones for one or more patients, and
  (vi) determine discharge milestones used most frequently on a unit of the health care facility and display, to a user, a report conveying the determined discharge milestones,
(c) receiving authentication information;
(d) validating the received authentication information;
(e) receiving, via the electronic-touch screen display, user input related to some of the displayed information associated with the provision of health care services to patients; and
(f) displaying, via the electronic touch-screen display, updated information associated with the provision of health care services to patients, the updated information being updated based at least in part on the received user input;
(g) wherein the electronic touch-screen display is not a part of a computer work station.

7. The method of claim 6, wherein said step of receiving authentication information comprises receiving, via an electronic card reader, authentication information.

8. The method of claim 6, wherein the software is further configured to display information in a tabular view that is configured to resemble a nursing unit whiteboard.

9. The method of claim 6, wherein a nursing unit whiteboard is disposed adjacent the electronic touch-screen display.

10. The method of claim 6, wherein the electronic touch-screen display is mounted to a wall.

11. A method for facilitating the physical provision of health care services to a plurality of patients, the method comprising:
(a) aggregating, at one or more electronic devices, information associated with the provision of health care services to patients from one or more systems, including an admission/discharge/transfer system and a bed management system;
(b) displaying, via software, at an electronic touch-screen display, some of the aggregated information, the software being configured to
  (i) display information associated with a housekeeping status of one or more beds in a health care environment, and allow a user to edit the displayed information associated with the housekeeping status of such one or more beds,
  (ii) allow a first administrative user associated with a health care facility to define a list of discharge milestones and indicate that one or more of the defined discharge milestones are required for all patients within the health care facility,
  (iii) allow additional administrative users each associated with a respective unit of the health care facility to each select, from the discharge milestones defined by the first administrative user, milestones specific to a particular unit,
  (iv) display information associated with a planned discharge time,
  (v) display information associated with one or more defined discharge milestones for each of a plurality of patients, and allow a user to edit the displayed information associated with one or more discharge milestones for one or more patients,
  (vi) determine discharge milestones used most frequently on a unit of the health care facility and display, to a user, a report conveying the determined discharge milestones, and
  (vii) determine the average time to completion of a discharge milestone compared to a planned discharge time and display, to a user, the determined average time;
(c) receiving authentication information;
(d) validating the received authentication information;
(e) receiving, via the electronic-touch screen display, user input related to some of the displayed information associated with the provision of health care services to patients; and
(f) displaying, via the electronic touch-screen display, updated information associated with the provision of health care services to patients, the updated information being updated based at least in part on the received user input;
(g) wherein the electronic touch-screen display is not a part of a computer work station.

12. The method of claim 11, wherein said step of receiving authentication information comprises receiving, via an electronic card reader, authentication information.

13. The method of claim 11, wherein the software is further configured to display information in a tabular view that is configured to resemble a nursing unit whiteboard.

14. The method of claim 11, wherein a nursing unit whiteboard is disposed adjacent the electronic touch-screen display.

15. The method of claim 11, wherein the electronic touch-screen display is mounted to a wall.

* * * * *